United States Patent [19]

Soma et al.

[11] Patent Number: 5,346,891

[45] Date of Patent: Sep. 13, 1994

[54] LIPOPOLYSACCHARIDE-PRODUCING BACTERIA, LIPOPOLYSACCHARIDES, AND LIPOPOLYSACCHARIDE-CONTAINING, MEDICINES AND VETERINARY MEDICINES

[75] Inventors: Gen-Ichiro Soma, 1-10-21, Higashi-Tamagawa, Setagaya Ward, Tokyo; Kiyoshi Yoshimura; Daisuke Tsukioka, both of Chiba; Den'ichi Mizuno, Okamoto-18, Kamakura City, Kanagawa; Haruyuki Oshima, Hachioji, all of Japan

[73] Assignees: Gen-Ichiro Soma, Tokyo; Den'ichi Mizuno, Kanagawa, both of Japan

[21] Appl. No.: 747,633

[22] Filed: Aug. 20, 1991

[30] Foreign Application Priority Data

Aug. 20, 1990 [JP] Japan .................................. 2-218599
Nov. 20, 1990 [JP] Japan .................................. 2-312932

[51] Int. Cl.⁵ ...................... A61K 31/715; C12N 1/00; C12N 1/20
[52] U.S. Cl. ...................... 514/54; 514/885; 435/243; 435/252.1; 435/252.5
[58] Field of Search ................... 514/54, 885; 435/243, 435/252.1, 252.5

[56] References Cited

U.S. PATENT DOCUMENTS

| | | | |
|---|---|---|---|
| 4,460,575 | 7/1984 | d'Hinterland et al. | 530/405 |
| 4,755,381 | 7/1988 | Cryz | 435/852 |
| 4,870,158 | 9/1989 | Karol et al. | 424/88 |
| 4,877,610 | 10/1989 | McMichael | 424/88 |
| 4,877,611 | 10/1989 | Cantrell | 514/885 |
| 4,892,862 | 6/1989 | Jacobs et al. | 424/88 |
| 4,980,160 | 12/1990 | Goldberg et al. | 530/351 |
| 4,980,455 | 12/1990 | Sakaguchi et al. | 530/351 |
| 5,023,820 | 6/1991 | Haranaka et al. | 530/350 |
| 5,057,598 | 10/1991 | Pollack et al. | 435/172.2 |

*Primary Examiner*—Douglas W. Robinson
*Assistant Examiner*—Deborah K. Ware
*Attorney, Agent, or Firm*—Spensley, Horn, Jubas & Lubitz

[57] ABSTRACT

Novel LPS having the following physical properties, novel bacilli providing those LPS, and novel immunity stimulators, anagesics, and antiwithdrawal agents, and novel veterinary immunity stimulators, analgesics, and antiwithdrawal agents containing LPS selected from the group consisting of those LPSs and mixtures thereof.

LPS1 Dominant molecular weight: 5,000±1,000 as determined by

| | SDS-PAGE method |
|---|---|
| Phosphorus number: | 2 ± 1/5,000 (m.w.) |
| Hexosamine number: | 9 ± 1/5,000 (m.w.) |
| KDO number: | 2 ± 1/5,000 (m.w.) |

LPS2 Dominant molecular weight: 6,500±2,500 as determined by

| | SDS-PAGE method |
|---|---|
| Phosphorus number: | 1 to 2/5,000 (m.w.) |
| Hexosamine number: | 7 ± 1/5,000 (m.w.) |
| KDO number: | 1 to 2/5,000 (m.w.) |

LPS3 Dominant molecular weight: 6,500±2,500 as determined by

| | SDS-PAGE method |
|---|---|
| Phosphorus number: | 2 ± 1/5,000 (m.w.) |
| Hexosamine number: | 5 ± 1/5,000 (m.w.) |
| KDO number: | 2 ± 1/5,000 (m.w.) |

6 Claims, 3 Drawing Sheets

LIPOPOLYSACCHARIDE-PRODUCING BACTERIA, LIPOPOLYSACCHARIDES, AND LIPOPOLYSACCHARIDE-CONTAINING, MEDICINES AND VETERINARY MEDICINES

FIELD OF THE INVENTION

The present invention relates to novel lipopolysaccharide-producing (LPS-producing) bacteria, novel lipopolysoccharides (LPSs) and lipopolysaccharide containing (LPS-containing) medicines and veterinary medicines.

More particularly, it is concerned with three novel glucose-fermentative gram-negative small bacilli which produce LPSs, novel LPSs provided by those bacteria, and novel immunostimulating agents, analgesics, antiwithdrawal agents, veterinary immunostimulating agents, veterinary analgesics and veterinary antiwithdrawal agents containing those LPSs.

DESCRIPTION OF THE PRIOR ART

Organisms have their own immunity to keep their internal conditions from being disturbed by exogenous or endogenous matter and to maintain their homeostasis. Thus, the lowering of immunity causes deterioration of health, occurrence of various diseases, stimulation of aging, etc. On the other hand, its activation leads to improvement of health, prevention against occurrence of various diseases, cure of various diseases and prevention of aging or the like.

For the above-mentioned, it has been desired to provide a substance capable of activating immunity. To date, PSK [another name: KRESTIN ® (trade name of Kureha Kagaku Co. in Japan and registered in Japan], LENTINAN ® (trade name of Ajinomoto Co. in Japan and registered in Japan), BESTATIN ® (trade name of Nihon Kayaku Co. in Japan and registered in Japan), SONIFILAN ® (trade name of Kaken Selyaku Co. in Japan and registered in Japan), OK-432 [Cancer Chemotherapy Reports Part 1, vol. 58, No. 1, p.10, 1972; another name: PICIBANIL ® (trade name of Chugai Seiyaku Co. in Japan and registered in Japan], etc. are known to have such capability.

Analgesics are classified into two groups; narcotic and nonnarcotic ones.

Narcotic analgesics are of course narcotics, and thus they are required to be administered with the greatest care. ("Clinical pains", pp. 70-74, 1981, Medical Friend Co. in Japan)

On the other hand, generally the analgesic action of non-narcotic analgesics is characterized to be less than that of narcotic ones and to be nonhabit-forming. But, actually their prolonged use is reported to cause tolerance and/or dependence of the patients thereto, and titus they are considered to be used in the same manner as narcotic-ones from pharmacological viewpoints. ("Clinical pains", p. 74, supra)

It is generally well known that the so-called withdraws symptoms occur when one is suddenly kept from taking alcohol, morphinic narcotics, nicotine, etc. to which he has become addicted. Also it is well known that addicts of them are hard to return to daily life, and the clinical use of narcotics is restricted because of withdrawal symptoms.

To date, methadone, clonidine, dizocilpine, etc. are known as medicines for suppressing such withdrawal symptoms. Methadone is, however, reported to cause dependence. (P. R. Dougherety, et al., "Neuropharmacology", 26, pp. 1595-1600, 1987) Clonidine is reported to suppress withdrawal body shake by intraperitoneal administration of 0.16 mg/kg. (Stuart Fielding, et al. "The Journal of Pharmacology and Experimental Therapeutics", vol. 207, No. 7, pp. 899-905, 1978) But, we the inventors, have found that lntravenous administration of clonidine fails to suppress jumping, a severe withdrawal symptom even at a dose of 0.1-10 mg/kg, and further causes convulsions at a dose of 10 mg/kg. Dizocilpine shows only an extremely small difference between its toxic and effective doses, and thus is not safe. (Keith A., et al., "Science", 251, pp, 85-87, 1991).

Of the prior art immunity stimulators, PSK, LENTINAN ® BESTATIM ® and SONIFILAN ® have no TNF productivity, and thus their immunity stimulation is poor.

Surely OK-432 is known to have TNF productivity, but a rather large quantity of it must be administered to produce a satisfactory quantity of TNF, thereby inevitably causing attack of fever or rigor, lowering of blood pressure, and reduction in the number of thrombocytes. Accordingly, OK-432 has a low therapeutic range. OK-432 has an additional drawback in that its production steps include culturing of microorganisms, and extremely complicated procedures for its separation and purification with the result of high production cost. Further, OK-432 fails to produce TNF through oral or subcutaneous administration which is very convenient for medication; therefore OK-432 must be administered by routes inconvenient for a host.

Here, the term "TNF" is the generic name for tumor necrosis factors produced by macrophage (*The Journal of Biol. Chem.*, 260, pp. 2345-2354, 1985), and the production quantity of TNF increases depending on the activity of macrophage. Macrophage is the generic name for large amoeba-like cells which belong to immunocompetent cells, are present in most internal tissues of animals, and prey and digest particulate foreign matter and waste cells in the body. The term "therapeutic range" is the ratio of the maximum tolerant dose of the host to the medicine to the minimum effective dose of the medicine; the larger the ratio is, the better the medicine is As mentioned above, the prior art analgesics have drawbacks, and no satisfactory ones have not been provided yet. Particularly, analgesics which are effective against chronic pain, are highly safe, have no side effects, are cheap and are very convenient for medication have been greatly expected to be developed. Also no satisfactory antiwithdrawal agents have not been provided yet.

The present invention is intended to provide novel immunity-stimulating agents, analgesic agents, antiwithdrawal agents, veterinary immunity-stimulating agents, veterinary analgesic agents and veterinary antiwithdrawal agents which are free from the drawbacks of the prior art.

An additional object of the present invention is to provide novel LPSs, active ingredients of those agents, which have excellent immunity-stimulating, analgesic and antiwithdrawal effects, show a high therapeutic range, and may be provided at a low cost and in a large amount and may be administered via any route of oral and intradermal administration and injection.

An additional object of the present invention is to provide novel bacteria which produce the novel LPSs.

DETAILED DESCRIPTION OF THE INVENTION

Bacteria-providing sources

Figure 1:
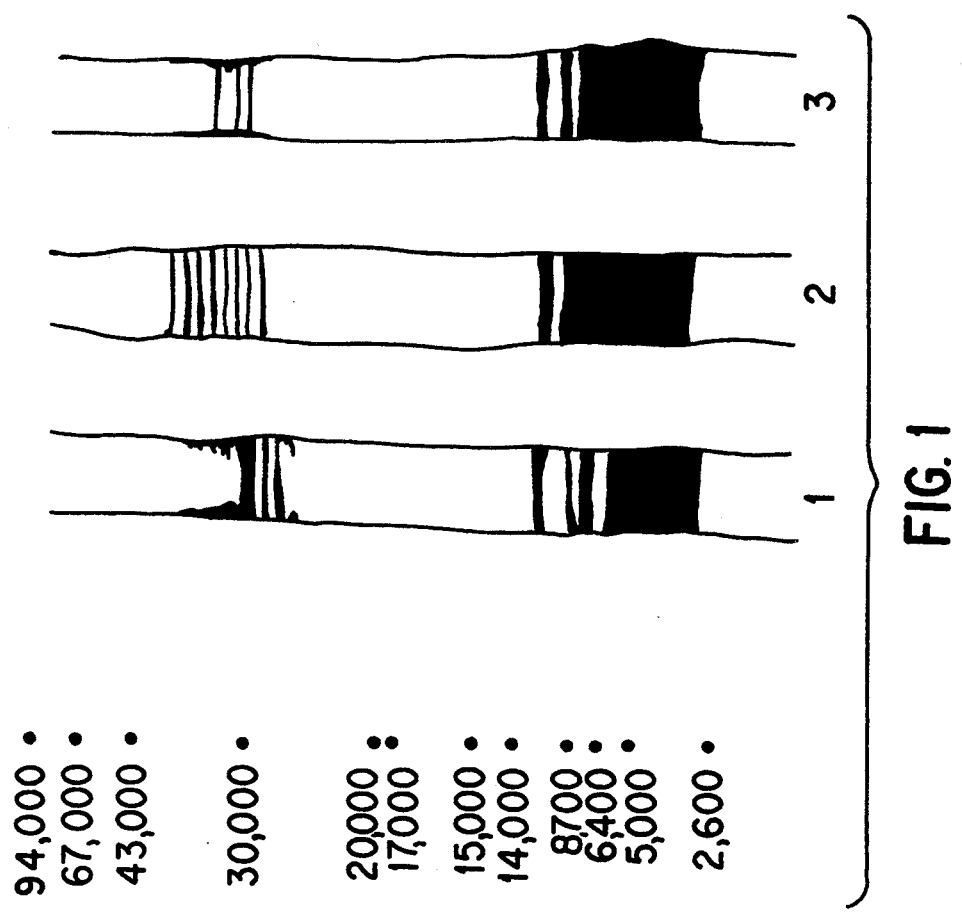
FIG. 1 is a chart showing the patterns of the LPSs of the present invention on SDS-PAGE method.

The three bacteria according to the present invention were isolated from all kinds of wheat investigated by the inventors of the present invention regardless of their places of production. Thus, those bacteria are supposed to be isolated from any kind of wheat produced in any place and its processed goods. The kinds and the places of production of the wheat flour from which the three bacteria mentioned above were isolated by the inventors of the present invention include the following:

| Kinds of wheat flour | Places of production |
| --- | --- |
| Dark Northern Springs | U.S.A. |
| 1 Canadian Wheat | Canada |
| Hard Red Winter Semi-hard | U.S.A. |
| Australian Standard Wheat | Australia |
| Horoshiri | Japan |

Isolation of LPSs

The LPSs of the present invention may be isolated from the above bacteria by the hot phenol process described on page 83 of Westphal, et al., "Methods In Carbohydrate Chemistry", vol. v, 1965, Academic press In New York, followed by purification on an anion-exchange resin.

The cells are suspended in distilled water which is then stirred with an equivolume of hot phenol. Next, the aqueous layer is recovered by centrifugation and then subjected to dialysis to remove off the phenol. The aqueous layer is concentrated by ultrafiltration to yield crude LPS fractions which are then purified conventionally, for example, by anion-exchange chromatography using MONO Q-SEPHAROSE and Q-SEPHAROSE in FPLC system (all manufactured by Pharmacia Inc.), followed by desalting in a conventional manner.

Products of 96% or higher purity are provided by the foregoing procedures.

Physical properties of LPSs

As explained in detail in the examples given later, the three LPSs of the present invention having a purity of 96% or more showed the following physical properties ("SDS-PAGE method will be defined later In Example 1):

LPS1 Dominant molecular weight: 5,000±1,000 as determined by

| | SDS-PAGE method |
| --- | --- |
| Phosphorus number: | 2 ± 1/5,000 (m.w.) |
| Hexosamine number: | 9 ± 1/5,000 (m.w.) |
| KDO number: | 2 ± 1/5,000 (m.w.) |

LPS2 Dominant molecular weight: 6,500±2,500 as determined by

| | SDS-PAGE method |
| --- | --- |
| Phosphorus number: | 1 to 2/5,000 (m.w.) |
| Hexosamine number: | 7 ± 1/5,000 (m.w.) |
| KDO number: | 1 to 2/5,000 (m.w.) |

LPS3 Dominant molecular weight: 6,500±2,500 as determined by

| | SDS-PAGE method |
| --- | --- |
| Phosphorus number: | 2 ± 1/5,000 (m.w.) |
| Hexosamine number: | 5 ± 1/5,000 (m.w.) |
| KDO number: | 2 ± 1/5,000 (m.w.) |

Forms supplied

The LPS5 of the present invention may be supplied as such or in forms concentrated to any desired degree. Further, they may be supplied as dry powders prepared by any of the conventional manners including lyophilization and spray drying to improve stability. Any of these forms may be produced conventionally.

Determination of immunity stimulation

The immunity stimulation of the LPSs according to the present invention has been confirmed by endogenous TNF productivity.

Carswell et al. report that priming and triggering steps are necessary to produce endogenous TNF in the body of an animal; see *Proc. Natl. Acad. Sci. USA.*, 72, pp. 3666–3670, 1975. Thereafter, many candidate chemicals were examined for their ability to stimulate the respective steps. The chemical used to start the priming step is a primer (endogenous TNF production stimulator), while that administered to start the triggering step is a trigger (endogenous TNF productive agent).

The TNF activity is determined, as follows, on the basis of the cytotoxicity to L929 cells (*Proc. Natl. Acad. Sci. U.S.A.*, 72, pp. 3886–3870, 1975). L-929 cells are cultured in Eagles' Minimum Essential Medium (hereunder referred to only as MEM) with 5% fetal calf serum (hereunder referred to only as FCS) added thereto until 100 $\mu$l of the medium contains $8 \times 10^4$ cells, and then the cells are grown in a flat-bottomed plate having 96 wells.

The growth conditions are 37° C. in the presence of 5% $CO_2$, and under a humidity of 100% for 2 hours, and the procedures may be the same as those employed in conventional cell culturing techniques. Then actinomycin D is added to the medium to a final concentration of 1 $\mu$g/ml, and the volume of the culture solution is adjusted to 150 $\mu$l. Immediately thereafter 50 $\mu$l of the sample diluted appropriately with MEM medium is added to the culture solution. Here, $ED_{50}$ may be determined by adjusting the dilution appropriately. The L-929 cells having a final volume of 200 $\mu$l are cultured for an additional 18 hours under the same conditions as described above.

In order to determine the cell necrosis activity, first the whole medium is removed followed by addition of a 1% methyl alcoholic solution containing 0.1% crystal violet for fixation staining, Crystal violet stains all the eukaryotic cells, but the dead cells are removed off from the bottom of the flask only by washing after the staining; so the cell necrosis activity may be determined directly. The staining degree is measured on the basis of adsorption at $OD_{590nm}$, and is compared with that of a control to determine the cell necrosis activity. This activity is defined as follows.

The dilution of the sample which allows 50% of the L-929 cells to survive (N) is determined. Rabbit TNS is used as the control, and its activity n (units/ml) is determined using $2.4 \times 10^6$ units/mg/ml of TNF-$\alpha$. The dilution which provides $ED_{50}$ of rabbit TNS (tumor necrosis serum) is determined.

The activity of the sample (units/ml) is calculated by the equation: $N/C \times n$.

Determination of Analgesic Effects

The analgesic effects of the LPSs of the present invention have been confirmed by an experiment using animals according to the acetic acid-writhing method described on page 415 of "Inflammation and anti-inflammatory therapy" issued in 1982 by Ishiyaku Shuppan Co. In Japan, one of the established methods for the determination of the effects of non-narcotic analgesics.

Determination of Antiwithdrawal Effects

The antiwithdrawal effects of the LPSs according to the present invention have been confirmed by the reduction in the frequency of jumping, the severest withdrawal symptom caused by the administration of naloxone to morphine-addictive mice. Naloxone is available from Endo Labs. Inc. in U.S.A., and is known to be a morphine antagonist; "The Journal of Pharmacology and Experimental Therapeutics", vol. 207, No. 7, p. 901, supra.

The LPSs according to the present invention may be used separately, and further may be used in admixture with each other or together with any other substance so far as the intended effects are not reduced. In addition, they may be included in immunity diagnostic reagents, veterinary immunity diagnostic reagents, quasi drugs defined In the Japanese Pharmacopoeia, cosmetics, food, drinks and feed.

Any of the above preparations including immunity stimulators may be produced conventionally. For example, in the conventional manner of preparing medicines or veterinary medicines, they may be supplied conventionally in the form of powders, granules, pills, tablets, troches, capsules, solutions, Pastes, ointments, liniments, lotions, suppositories, injections, etc. Paticularly, many macrophages are present In the skin, so the LPSs of the present invention may be prepared as skin ointments in order to obtain better effects. For veterinary use, also the agents may be prepared in the form of feed additives, premix preparations, drinking water additives. Here, the "premix preparations" are those which contain feed components beforehand so that they are easily mixed in the feed. The feed additives are preferably powders or granules. Any commercially available feed may be used to prepare the above -mentioned feed additives, premix preparations, etc. The feed may contain minerals, vitamins, amino acids and any other feed additives.

If desired, these preparations may contain excipients, preservatives, buffers, etc. conventionally to improve the shelf life, homogeneity, etc. In addition, the preparations may contain correctives to Improve taste, odor, appearance, etc. The excipients include, for example, lactose, starch, etc. The preservatives include, for example, parahydroxybenzoic esters such as methyl, ethyl or propyl paraoxybenzoate, sodium dehydroacetate, phenols, methyl, ethyl or propylparabene, etc. The buffers Include, for example, citric, acetic or phosphoric acid salts, etc.

Hereunder, the present invention will be explained in detail with reference to examples, preparations and experiments. The *E. coli* LPS used therein is available from Difco Co. in U.S.A. under the code number of 0128:B8.

EXAMPLE 1

1) In a 50 ml coning tube, there was charged 1.04 g of hard flour containing 1.09% of ash (1 Canadian wheat from Canada) followed by addition of 20 ml of distilled water thereto to prepare a 50 mg/ml aqueous solution of wheat flour.

2) The solution was cultured in a water bath at 37° C. while shaking, and 0.5 ml portions of the solution were collected at 0, 1, 2, 3, 4, 6, 8, 10, 12, 20, 24 and 45 hours thereafter. 100 μl portions of the respective solutions diluted to 1 to 100,000 times were taken in standard agar culture media available from Nissui Seiyaku Co. In Japan and having the following composition to determine the number of living cells and to observe the colonies.

Standard agar culture media (Nissui Seiyaku's code No.: 05618)

| | |
|---|---|
| Yeast extracts | 2.5 g/l |
| Peptone | 5.0 g/l |
| Glucose | 1.0 g/l |
| Agar | 15.0 g/l |
| pH | 7.1 ± 0.1 |

At the end of 8 and 10 hours culturing, yellow to creamy opaque colony (colony 1), creamy opaque colony (colony 2) yellow translucent colony (colony 3), milk white opaque colony (colony. 4), and white opaque small colony (colony 5), which were .judged to be different from each other, were scattered on the respective standard agar culture having the same composition as the above, for subcultivation. The gram staining and limulus activity of the bacteria in the colonies were determined.

Here, the "limulus activity" means positive to limulus test which is a method invented by Levin in 1968 for quantitative determination of endotoxin using a horseshoe crab haemocyte extract and a chromogenic substrate. The limulus test is known as a method for the detection of LPSs, and may be carried out using, for example, a reagent set commercially available from Sei-Kagaku Kogyo Co. in Japan under the trade name of TOXI COLOR SYSTEM ®.

Of the above colonies, the limulus activity of the colonies 4 and 5 (both being gram stain-positive) were extremely low as compared with that of the colonies 1, 2 and 3 (all being gram stain-negative), so the former colonies were taken aside. The morphological and biochemical characteristics of only the colonies 1, 2 and 3 were observed using the media available from Nissui Seiyaku Co. and ID tests EB-20 to show the following results:

Bacteria forming the colony 1 (ID number: 900814-1)

(The bacteria were deposited with Fermentation Research Institute Agency of Industrial Science and Technology on Aug. 17, 1990 under the number of FERM P-11664 and transferred to the international deposit under BUDAPEST TREATY on Aug. 12, 1991 under the number of FERM BP-3509.)

The bacteria are supposed to belong to a strain of the species *Serratia ficaria* of the family Enterobacteriaceae in view of the following morphological and biochemical characteristics.

a) Morphological characteristics
1) Small rod
2) No Motility
3) Gram stain: − b) Growth
1) Standard agar medium: a yellow to creamy round opaque colony is formed.
2) SS agar medium: A white translucent colony is formed. [SS agar medium: Nissui Seiyaku's code No. 05031]

|  |  |
|---|---|
| Broth | 5.0 g/l |
| Bile acid salts | 9.0 g/l |
| Peptone | 7.5 g/l |
| Lactose | 10.0 g/l |
| Sodium citrate | 8.5 g/l |
| Sodium thiosulfate | 5.5 g/l |
| Ferric citrate | 1.0 g/l |
| Neutral red | 0.025 g/l |
| Brilliant green | 0.033 g/l |
| Agar | 13.5 g/l |
| pH: | 7.1 ± 0.1 |

3) TSI agar medium: No change is found on the slant, but the higher layer changes to yellow. Gas is produced. [SS agar medium: Nissui Seiyaku's code No. 05031]

|  |  |
|---|---|
| Broth | 5.0 g/l |
| NaCl | 5.0 g/l |
| Peptone | 15.0 g/l |
| Lactose | 10.0 g/l |
| Sucrose | 10.0 g/l |
| Glucose | 1.0 g/l |
| Ferric citrate | 0.2 g/l |
| Sodium thiosulfate | 0.2 g/l |
| Phenol red | 0.02 g/l |
| Agar | 15.0 g/l |
| pH: | 7.6 ± 0.1 | c) Physiological characteristics
1) Voges-Proskauer reaction: +
2) Indole production: −
3) Hydrogen sulfide production: −
4) Utilization of citrate: +
5) Urease: −
6) Oxidase: −
7) O-F test: + d) Utilization of carbon sources
1) Lactose: +
2) Adonitol: −
3) Rhamnose: +
4) Mannitol: +
5) Esculin: +
6) Inositol: −
7) Sorbitol: +
8) Arabinose: +
9) Raffinose: +
10) Sucrose: + e) Others
1) Lysin decarboxylase: −
2) Utilization of malonate: −
3) Arginine dihydroxylase: −
4) Phenylalanine deaminase: −
5) Ornithine decarboxylase: −

Bacteria forming the colony 2 (ID number: 900814-2)

(The bacteria were deposited with Fermentation Research Institute Agency of Industrial Science and Technology on Aug. 17, 1990 under the number of FERM P-11665 and transferred to the international deposit under BUDAPEST TREATY on Aug. 12, 1991 under the number of FERM BP-3510.)

The bacteria are supposed to belong to a strain of the species *Enterobacter cloacae* of the family Enterobacteriaceae in view of the following morphological and biochemical characteristics.

a) Morphological characteristics
1) Small rod
2) No Motility
3) Gram stain: − b) Growth
1) Standard agar medium: a creamy opaque colony is formed.
2) SS agar medium: A red opaque colony is formed.
3) TSI agar medium: No change is found on tile slant, but the higher layer changes to yellow. Gas is produced.

c) Physiological characteristics
1) Voges-Proskauer reaction: +
2) Indole production: −
3) Hydrogen sulfide production: −
4) Utilization of citrate: +
5) Urease: −
6) Oxidase: −
7) O-F test: + d) Utilization of carbon sources
1) Lactose: +
2) Adonitol: −
3) Rhamnose: +
4) Mannitol: +
5) Esculin: +
6) Inositol: −
7) Sorbitol: +
8) Arabinose: +
9) Raffinose: +
10) Sucrose: + e) Others
1) Lysin decarboxylase: −
2) Utilization of malonate: +
3) Arginine dihydroxylase: +
4) Phenylalanine deaminase: −
5) Ornithine decarboxylase: +

Bacteria forming the colony 3 (ID number: 900814-8)

(The bacteria were deposited with Fermentation Research Institute Agency of Industrial Science and Technology on Aug. 17, 1990 under the number of FERM P-11666 and transferred to the international deposit under BUDAPEST TREATY on Aug. 12, 1991 under the number of FERM BP-3511.)

The bacteria are supposed to belong to a strain of the species *Pantoea agglomerans* of the family Enterobacteriaceae in view of the following morphological and biochemical characteristics.

a) Morphological characteristics
1) Small rod
2) No Motility
3) Gram stain: −
b) Growth
1) Standard agar medium: A yellow round translucent colony is formed.
2) SS agar medium: No colony is formed.
3) TSI agar medium: No change is found on the slant, but the higher layer changes to yellow. Gas in not produced.
c) Physiological characteristics
1) Voges-Proskauer reaction: +
2) Indole production: −
3) Hydrogen sulfide production: −
4) Utilization of citrate: +
5) Urease: −
6) Oxidase: −
7) O-F test: +
d) Utilization of carbon sources
1) Lactose: +
2) Adonitol: −
3) Rhamnose: +
4) Mannitol: +
5) Esculin: +
6) Inositol: −
7) Sorbitol: +
8) Arabinose: +
9) Raffinose: −
10) Sucrose: +
e) Others
1) Lysin decarboxylase: −
2) Utilization of malonate: +
3) Arginine dihydroxylase: −
4) Phenylalanine deaminase: −
5) Ornithine decarboxylase: −

4) The colonies 1, 2 and 3 were transferred to 1 liter L-broth medium, respectively, and the media were shaken at 37° C. over night, and then subjected to centrifugation at 5,000 G, 4° C. for 20 minutes to collect the cells. The L-broth was prepared by dissolving 10 g of polypeptone (Difco Co.), 5 g of yeast extracts (Difco Co.) and special grade NaCl (Wako-Jun-Yaku Co. in Japan) in distilled water, adjusting the pH of the solution to 7.5 with NaOH followed by autoclaving, and then adding a 400-fold diluent of a 40% solution of special grade glucose (Wako-Jun-Yaku Co.) to the solution.

5) The cells of the respective colonies were suspended in 50 ml of distilled water, and 50 ml of a 90% hot phenol was added to the suspension followed by stirring at 65°-70° for 20 minutes. After being cooled, the mixture was subject to centrifugation at 10,000 G, 4° C. for 20 minutes to recover the aqueous layer. The phenol layer was treated additional two times in the same manner as the above. The combined three aqueous layers were subjected to dialysis overnight to remove the phenol. The inner solution was subjected to ultrafiltration using UK-20 (Advantec Toyo Co.) for concentration by cutting off molecular weight 200,000; $N_2$ pressure: 2 atms.

6) The concentrated sample was subjected to anion-exchange chromatography using Q-SEPHAROSE FAST FLOW® (Pharmacia Co.). That is, the sample was applied to the column using a buffer solution containing 10 mM Tris-HCl (pH 7.5) and 10 mM of NaCl, and then the limulus active fractions were eluted with 400 mM NaCl/10 mM Tris-HCl (pH 7.5). The eluate was subjected to ultrafiltration under the same conditions as the above for desalting and concentration to produce 96% or more pure LPS. The nucleic acid was eluted with 1M NaCl/10 mM Tris-HCl (pH 7.5).

The results of the respective cells are shown in Tables 1-3. Here, the LPS content is in terms of *E. coli* LPS. The sugar content was determined according to the phenol—sulfuric acid method (M. Dubis et al., "Analytical Chemistry", vol. 28, p. 350, 1956), while the protein content was determined by the Lowry method (O. H. Lowry et al., "Journal of Biological Chemistry), vol. 193, p. 65, 1951. The nucleic acid content was determined on the basis of the measurements of OD at 260 nm (1 OD=50 μg), and the purity (%) was calculated by the equation:

$$\text{Purity} = \frac{\text{Dried yield} - (\text{Protein yield} + \text{nucleic acid yield})}{\text{Dried yield}} \times 100$$

TABLE 1

| 900814-1 | |
|---|---|
| Total dried yield (mg) | 6.8 |
| LPS (mg) | 19.8 |
| Sugar (mg) | 3.1 |
| Protein (μg) | 86 |
| Nucleic acid (μg) | <161 |
| Purity (%) | 96< |

TABLE 2

| 900814-2 | |
|---|---|
| Total dried yield (mg) | 10.4 |
| LPS (mg) | 75.6 |
| Sugar (mg) | 2.5 |
| Protein (μg) | 64 |
| Nucleic acid (μg) | <108 |
| Purity (%) | 98< |

TABLE 3

| 900814-3 | |
|---|---|
| Total dried yield (mg) | 19.2 |
| LPS (mg) | 103.6 |
| Sugar (mg) | 7.6 |
| Protein (μg) | 73 |
| Nucleic acid (μg) | <137 |
| Purity (%) | 99< |

6) Molecular weight

The LPSs resulting from the respective cells were dissolved in distilled water, respectively to prepare solutions containing 2 mg/ml of LPSs. The 10 μl portions of the solutions were placed in 1.5 ml plastic tubes. To the respective portions there was added 10 μl of an SDS treatment solution prepared by mixing 10 μl of 10% (w/v) of SDS, 45 μl of 5% β-mercaptoethanol, 90 μl of a CBB coloring matter solution, 112.5 μl of 0.5M Tris-HCl (pH 6.8) and 22.5 μl of distilled water. The resulting mixture was mixed well and then immersed in boiling water for 5 minutes, and immediately thereafter the mixture was quenched in ice water.

10 ml of 10% (w/v) SDS, 17.9 g of tricine and 3.03 g of Tris were dissolved in 1 liter of distilled water to prepare a buffer solution for electrophoresis which was then placed in Slab-gel electrophoresis tank (Marisoru Co.). polyacrylamide gel (20%) was fixed in the tank, and the sample was placed in the sample groove. The voltage was kept at 50 v for 1 hour, and then at 150 v, and the electrophoresis was allowed to proceed until the coloring matter flowed out through the gel; these procedures are defined as SDS-PAGE method throughout the specification and the claims. At the end of the electrophoresis, silver staining was carried out using silver staining kit 161-0443 (Bio-rad Co.) at room temperature to confirm the behavior.

The molecular weight of the LPSs of the present invention was calculated to be 5,000±1,000 (LPS1 resulting from bacteria 900814-1), and 6,500±2,500 (LPS2 and LPS3 resulting from bacteria 900814-2 and 900814-3, respectively) in view of the behaviors of the markers for protein m. w. [Pharmacia's LMW kit E: phosphorirase b (94k), albumin (67k), ovalbumin (43k), carbonic anhydrase (30k)', trypsin inhibitor (20k), α-lactalbumin (14k)], and those of the markers for peptide m. w. [Pharmacia's 1860-101 m. w. marker: myoglobin (16.9k), myoglobin I and II (14.4k), myoglobin I (8.2k), myoglobin II (6.0k) and myoglobin IV (2.5k). In the same manner as the above, $E.$ $coli$ LPS (0127:B8LPS available from Difco Co.) was found to have dominant m. w. at 40,000±10,000 and 8,000±4,000.

The stained bands of LPS1, LPS2 and LPS3 in the silver staining are shown in FIG. 1. In FIG. 1, the number 1, 2 and 3 show the stained bands of LPS1, LPS2 and LPS3, respectively. As shown in FIG. 1, LPS1 showed another stained band around m. w. 30,000. LPS2 showed another stained band bridging from 30,000 to 43,000, but it may be said that it contains only little high molecular weight substance in view of the staining strength of the bands at 14,000 or less. Also in view of the sugar content and hexosamine content mentioned later, LPS2 the lowest sugar content, and LPS1 has higher sugar content than LPS3. This order is believed to be in harmony with the patterns observed in the electrophoresis. Further, the ratio of LPS content to total dried yield decreases in the order of LPS2, LPS3 and LPS1. Considering the foregoing, it may be estimated that LPS2 comprises relatively low molecular weight LPSs, and the content of low molecular weight LPSs decrease in the order of LPS3 and LPS1.

7) Phosphorus content

The captioned content was determined as follows according to the Chen-Toribara method (Chen et al., "Analytical Chemistry", vol. 28, PP. 1756-1758, 1956)

LPS1, LPS2 and LPS3 were dissolved In distilled water separately to prepare 20 μl solutions containing 31.6, 57.6, or 103.6 μg of LPS which were then placed in a small test tube. To the mixture there was added 20 μl of 50 v/v sulfuric acid followed by heating at 160° for 2 hours. Then 20 μl of 50 v/v % perchloric acid was added to the mixture which was then heated on a gas burner for 1 minute to ash. Thereafter, 0.5 ml of distilled water and then 0.5 ml of a reaction reagent (a portion of the preparation made by mixing 1 ml of 6N sulfuric acid, 2 ml of distilled water, 2 ml of 2.5 v/w % ammonium molybdate and 1 ml of 10 v/w % of ascorbic acid) were added to the heated mixture which was then allowed to stand for 30 minutes at room temperature. Thereafter the absorption at 820 nm ($OD_{820nm}$) was determined. Here, as the standard sample for the preparation of the calibration curve, potassium dihydrogen phosphate (manufactured by Wako Jun-yaku Co. in Japan) was diluted with water to prepare 0.5 ml of solutions containing 2.5 μg, 1 μg, 0.25 μg or 0 μg of phosphorus. In this connection, 1 g of phosphorus corresponds to 4.39 g of potassium dihydrogen phosphate. The effects observed are shown in Table 4 given below.

In the table, the data of absorption are modified by subtracting the values of the control not subjected to the heating from the observed values in order to avoid occurrence of errors due to mixing-in of Inorganic phosphorus from, for example, phosphate buffer solution. The P content (μg) is calculated on the basis of the data of absorption. The P content (w/w %) was calculated according to the following equation. In the equation, "0.67" is the OD value of 1 μg of the standard phosphorus, and the sample concentration is the proportion of the respective LPSs dissolved in distilled water (mg/ml).

$$P \text{ content (w/w \%)} = \frac{\text{Absorption of sample}}{0.67 \times (\text{sample concentration}) \times 0.05}$$

P number is the number of phosphorus per m. w. 5,000 calculated according to the following equation:

$$P \text{ number} = \frac{P \text{ content (w/w \%)}}{100} \times \frac{5.000}{31}$$

TABLE 4

| LPS | Absorption | P content (μg) | P content (w/w %) | P number |
|---|---|---|---|---|
| 1 | 0.36 | 0.54 | 1.7 | 2 ± 1 |
| 2 | 0.31 | 0.46 | 0.8 | 1~2 |
| 3 | 0.87 | 1.30 | 1.3 | 2 ± 1 |

8) Hexosamine content

The captioned content was determined as follows according to the Elson-Morgan method (Library of biochemical experiments, No. 4, pp. 377–379, Tokyo Kagaku Dojin Shuppan Co. in Japan). LPS was dissolved in distilled water to prepare a solution containing 1.58 mg/ml of LPS1, 2.88 mg/ml of LPS2 or 5.18 mg/ml of LPS3, and the respective 100 μg portions were placed in a test tube with a screwcap (manufactured by Iwakl Glass Co. in Japan) followed by addition of 100 μl of 8N HCl thereto, and the mixture was heated at 110° C. for 16 hours, and then about 200 μl of 4N NaOH was added to tile mixture to bring the pH to 7. A 100 μl portion of the mixture was separated off and placed in another test tube with a screwcap followed by addition of 200 μl of Reagent A explained below thereto. The mixture was then heated at 105° C. for 1.5 hours, and then cooled with a running water. Next, a 100 μl portion of the mixture was separated off followed by addition of 670 μl of a 96% ethanol and then 67 μl of Reagent B explained below, and was then allowed to stand at room temperature for 1 hour followed by determination of adsorption at 535 nm. As the standard sample to prepare the calibration curve, 0.20–200 μg/ml of N-acetyl glucosamine (Wako Jun-yaku Co. in Japan) was used.

Reagent A: prepared by mixing 75 μl of acetyl acetone and 2.5 ml of 1.25N sodium carbonate Reagent B: prepared by mixing 1.6 g of p-dimethyl benzaldehyde, 30 ml of conc. hydrochloric acid and 30 ml of 96% ethanol As a result, the number of hexosamine in LPS1, LPS2 or LPS3 was 9±1, 7±1 or 5±1 per m. w. 5,000.

9) KDO content

The KDO (2-keto-3-dcoxyoctonate) content was determined as follows on the basis of the diphenylamine method (Shaby R. et al., "Analytical Biochem.", 58(1), pp. 123–129, 1974).

A KDO detection reagent was prepared by combining 500 mg of dipenylamine, 5 ml of ethanol, 45 ml of glacial acetic acid and 50 ml of conc. hydrochloric acid (all commercially available from Wako-junyaku Co. in Japan). A 500 µl portion of the prepared reagent was combined with 250 µl of distilled water containing any of 0.505 mg/ml of LPSI, 0.576 mg/ml of LPS2 and 0.518 mg/ml of LPS3. The resulting mixture was heated in a boiling water bath at 100° C. for 33 minutes and then cooled in cooling water at 24.5° C. for 30 minutes. The UV absorption of the mixture was determined at 420, 470, 630 and 650 nm to provide data $A_{420}$, $A_{470}$, $A_{620}$ and $A_{650}$, respectively. As the standard sample, there was used 250 µl of distilled water containing 0.5 µmole/ml of ammonium salt of KDO (Sigma Co. in U.S.A.). The value S for the test and standard samples was calculated according to the following equation:

$$S = A_{420} - A_{470} + A_{630} - A_{650}$$

The value of the test sample ($S_t$) was 0,109 for LPS1, 0,078 for LPS2 and 0.099 for LPS 3, whereas that of the standard sample ($S_s$) was 0.246. The value of distilled water was 0.005. The comparison of these values suggests that LPS1, LPS2 and LPS3 contain $2\pm1$, $1\sim2$ and $2\pm1$ of KDO per m. w. 5,000.

As an example, in the case of LPS1, the KDO content of the solution x (µmole/ml) may be determined by the equation:

$$\frac{0.5}{0.246} = \frac{x}{0.109}$$

According to the above equation, x is determined to be 0,221, Thus the molar number of KDO contained in 1 mole of LPS1 is determined to be 2.19 according to the following equation on the assumption that 1 mole of LPS1 is m. w. 5,000.

$$y = x \times 10^{-6} \times \frac{5,000}{0.505 \times 10^{-3}} = 2.19$$

Illustrative embodiments of preparations containing LPS according to the present invention will be given in the following examples wherein the LPS content is in terms of E. coli LPS calculated according to the limulus test.

| Example 2 (tablets) | |
| --- | --- |
| LPS1 | 0.04 g |
| 6% HPC lactose | 178 g |
| Talc stearate | 8 g |
| Potato starch | 14 g |

The above ingredients were mixed and formed into 400 tablets each weighing 0.5 g and containing 0.1 mg of wheat LPS1.

| Example 3 (solution for internal use) | |
| --- | --- |
| LPS1 | 1 mg |
| Purified water | 100 ml |

| Example 4 (ointment) | |
| --- | --- |
| LPS1 | 0.1 g |
| Purified lanolin | 80 g |
| Yellow petrolatum | ad 1,000 g |

| Example 5 (injection) | |
| --- | --- |
| LPS1 | 0.5 mg |
| Distilled water for injection | ad 1,000 ml |

Preparation 723 1 (preparation of B. pertussis LPS)

An experimental B. pertussis solution obtained from Serum Laboratory, a public institute of Chiba prefecture in Japan ($2.0 \times 10^{10}$ cells/ml) was used.

The solution was suspended in sterile water to prepare a suspension containing 25 mg (dry basis)/ml of dead cells. To the suspension, there was added an equivalent of a 90% hot phenol solution (68°-70° C.) was added, and the mixture was shaked at 68° C. for 1 hr. The mixture was subjected to centrifugation at 8,000 G, 4° C. for 20 min. to collect the aqueous layer. Sterile water in the same quantity as of the aqueous layer was added to the remaining phenol, and the mixture was shaked in the same manner as the above. The resulting aqueous layer was combined with the first aqueous layer followed by dialysis in running water overnight, and then the mixture was concentrated to a tenth using a rotary evaporator. The concentrate was subjected to centrifugation at 8,000 G, 4° C. for 20 min. The supernatant was separated off, and a small amount of sodium acetate was added thereto. Cold ethanol at 0°-4° C. was added to the mixture In an amount of six times as much as the latter, and the resulting mixture was allowed to stand at $-20°$ overnight. Then the mixture was subjected to centrifugation at 4,000 G, 4° C. for 30 min. to collect the sediment which was subjected to centrifugal washing with ethanol (twice) and acetone (once) followed by drying with an aspirator. The residue was suspended in distilled water to prepare a 20 mg/ml of solution which was then subjected to ultrasonic treatment with SONIFIa 185 ® (Branson Co. in U.S.A.) (outlet control 5, 15 min., room temperature). The solution was subjected to centrifugation at 2,500 G, 4° C. for 10 min. to separate off the supernatant.

The supernatant was treated at 4° C. with nucleases, DNase I and RNase A (both manufactured by Sigma Co. in U.S.A) for 15-16 hrs; totally 10 µg/ml of DNase I and 20 µg/ml of RNase A were used. The same amount of the nucleases as the above were added to the mixture followed by warming at 37° C. for 2 hrs and centrifugation at 2,500 G, 4° C. for 10 min. to separate off the supernatant.

The supernatant was filtered through a pore size of 0.2 µm using Acrodisc manufactured by Gelman Co. in U.S.A. The filtrate was subjected to molecular sieve (resin: SEPHAROSE 6B ® manufactured by Pharmacia Co. in U.S.A; column size: 5 cm (i.d.) $\times 100$ cm (length): buffer: 10 mM of Tris-HCl/10 mM of NaCl (pH 7.5); flow rate: about 3 ml/cm²/hr.). The fractions confirmed to be positive to limulus test with LS-1 kit commercially available from Sei-Kagaku Kogyo Co. in Japan were collected and filtered through a pore size of 0.2 µm using Acrodisc mentioned above. The filtrate was subjected to ion exchange (apparatus: FPLC manufactured by Pharmacia in U.S.A.; resin: MONO Q HR 10/10 ® manufactured by Pharmacia in U.S.A.; buffer: 10 mM of Tris-HCl/10 mM of NaCl (pH 7.5); flow rate: 2 ml/min.) wherein the filtrate was washed with the buffer for 15 min., then, after the NaCl content of the buffer was increased to 165 mM, for 30 min., then, for 20 min. while increasing the NaCl content to provide a NaCl content gradient from 165 mM to 1M, and then, for 30 min. at the NaCl content of 1M. The fractions confirmed to be positive to limulus test with LS-1 kit commercially available from Sei-Kagaku Kogyo Co. in Japan were collected.

The collected fractions were combined and desalted on a column (resin: SEPHADEX G-25 ® fine manufactured by Pharmacia in U.S.A.; column size: 2 cm (i. d.) ×25 cm (length); eluting agent: distilled water), and then lyophilized.

Nucleic acid may be mixed in the lyophilized sample (4.50 mg). Therefore, the UV absorption curve (200–400 nm) was prepared, and the absorbance at 260 nm was determined. The nucleic acid content was calculated to be 1% or less on the basis of the above absorbance in view of the fact that the nucleic acid content was 50 μg/ml in the case where the absorbance was 1. In addition, no apparent evidence showing the presence of a protein was observed in SDS electrophoresis. Thus, considering the detection sensibility, the highest content of proteins which may be mixed in the above lyophilized sample was estimated to be 0–3%. Accordingly, the purity of the above lyophilized sample was estimated to be 96% or more. The physical properties of the thus prepared B. pertussis LPS (sometimes referred to only as B. P. LPS) were determined in the same manner as described in Example 1. The results were as follows:

Physical properties of B. pertussis LPS

Molecular weight: 6,000±1,000 (by SDS-PAGE method)
Phosphorus content: 4 per molecular weight of 6,000
Hexosamine content: 12 per molecular weight of 6,000
Fatty acid content: 4 per molecular weight of 6,000
KDO content: 2±1 per molecular weight of 6,000

The physical properties of E. coli LPS (0128: B8 manufactured by Difco Co. in U.S.A.) determined in the same manner as described in Reference Example 1 were as follows:

Physical properties of E. coli LPS

Molecular weight: 40,000±10,000 8,000±4,000 (by SDS-PAGE method)
Phosphorus content: 12 per molecular weight of 30,000
Hexosamine content: 45±6 per molecular weight of 30,000
Fatty acid content: 18 per molecular weight of 30,000
KDO content: 5±1 per molecular weight of 30,000

Experiment 1 (immunostimulating effects)

1) Zero point two ml of physiological saline containing 1, 10 or 100 μg (in terms of limulus activity) of LPS1, LPS2 or LPS3 was injected into 7 week old C3H/He male mice via caudal vein; each group consisted of two or three mice having an average weight of 25 g. One hour later the serum was collected to determine the TNF activity on the basis of the toxicity to L929 cells. The results calculated as an average of two or three per group are shown in Table 5 given below. In the table, parenthesized are the number of the mice used.

TABLE 5

| Dose | TNF activity (units/ml) | | |
|---|---|---|---|
| | 1 μg | 10 μg | 100 μg |
| LPS1 | 6.15 (3) | 25.80 (2) | 30.69 (2) |
| LPS2 | 1.90 (3) | 7.47 (2) | 6.57 (2) |
| LPS3 | 7.44 (3) | 16.19 (2) | 34.47 (2) |

Experiment 2 (Analgesic effects)

To five-membered groups of 7 to 10 week old C3H/He male mice having an average body weight of 28 g, there was orally administrated 200 μl of distilled water containing 0, 1, 5, 25 or 400 μg/mouse of LPS3 or E. coli LPS using a probe. One and a half hours later, 500 μl of 0.7% acetic acid was given to the mice intraperitoneally over a period of 5 minutes The frequency of writhing of the respective mice was counted, for 30 minutes and the results as shown in Table 6 were recorded (an average of 5 mice in the respective groups). In the table, "—" reflects that the determination was not made at said dose. The writhing inhibition (%) was calculated by the following equation.

{1-[(frequency of writhing at the dose)-(that at 400 μg)]/ [(frequency of writhing at 0 μg)-(that at 400 μg)]}×100

TABLE 6

| LPS dose (μg/ mouse) | LPS3 of the present invention | | E. coli LPS | |
|---|---|---|---|---|
| | Writhing frequency | Writhing inhibition (%) | Writhing frequency | Writhing inhibition (%) |
| 0 | 18 | 0 | 20 | 0 |
| 1 | 17 | 10 | 18 | 82 |
| 5 | 10 | 80 | — | — |
| 25 | 7 | 110 | 13 | 64 |
| 400 | 8 | 100 | 9 | 100 |

Figure 2:
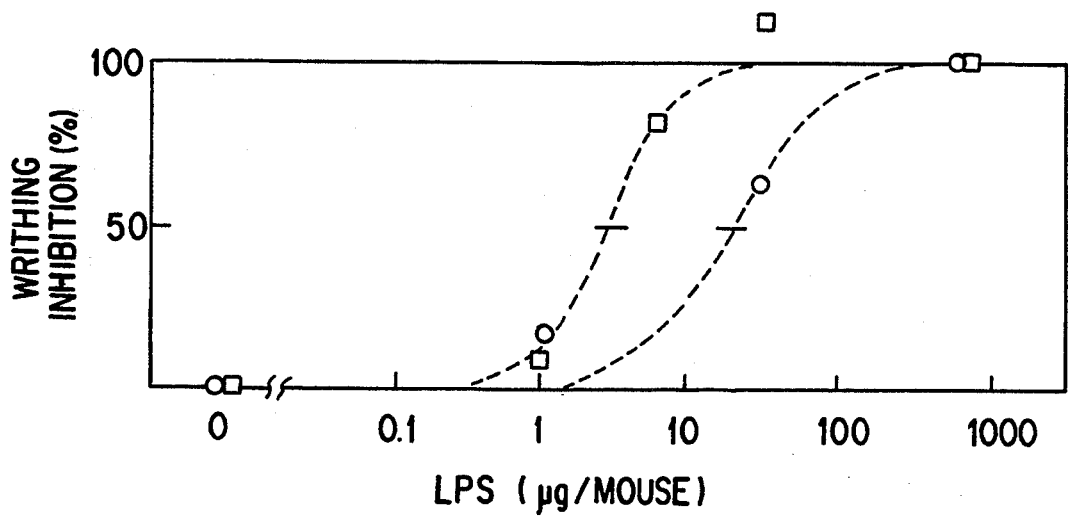
FIG. 2 is a graph showing the analgesic effects of the LPSs of the present invention in comparison with *E. coli* lipopolysaccharide (LPS).

FIG. 2 is a graph reflecting the results shown in Table 6.

FIG. 2 shows that the writhing inhibition $ED_{50}$ of LPS3 is 2.8 μg/mouse, whereas that of E. coli LPS is 17 μg/mouse. Thus it is supposed that the analgesic effect of LPS3 is about six times as of E. coli LPS.

Experiment 3 (Antiwithdrawal effect - 1)

Molecular sieves were impregnated with morphine HCl available from Takeda Chemical Industries Ltd. in Japan to prepare 12.7 mg of morphine pellet which was then implanted in the back, a little below the neck, of 4 to 5 week old ddY mice (body weight: 20–24 g). Two days later, there was given 50 μg/kg of E. coli LPS (6 mice), LPS3 (7 mice) or B.P. LPS prepared in Preparation 1 (6 mice) as a solution in physiological saline. The control group received only physiological saline. One hour later, 10 mg/kg of naloxone was given intraperitoneally, and immediately thereafter the jumping frequency of the mice was counted over a period of 40 minutes to determine the jumping control effects. The results are shown in Table 7. In the table, the figures show the number of the mice concerned. The jumping control effects were evaluated as follows:

The average jumping frequency of the control group (12 mice) per mouse was 62.7±25.5. So, in view of the difference 37 (=62.5-25.5), the case where the jumping frequency was 37 or more was estimated to have "no effect", whereas the case where the frequency was less than 37 was estimated to be "effective".

TABLE 7

|  | Jumping inhibition effect | |
| --- | --- | --- |
|  | Effective | No effect |
| Physiological saline | 1 | 11 |
| LPS3 | 7 | 0 |
| E. coli LPS | 3 | 3 |
| B.P. LPS | 4 | 2 |

As is apparent In Table 7, the antiwithdrawal inhibition ratio was only about 8% in the control group, whereas the value was 50 %, about 67% or 100% in the group to which E. coil LPS, B.P. LPS or LPS3 was given.

Experiment 4 (Antiwithdrawal effect - 2)

In order to determine whether the antiwithdrawal effects of the LPSs of the present invention in intravenous administration are dose-dependent, 12.7 mg of morphine pellet prepared as in Experiment 3 was implanted in the back, a little below the neck, of 4 to 5 week old ddY mice (average body weight: 20 g). Two days later, there was given 0.5 (to 6 mice ), 5 (to 6 mice), 15 (to 9 mice), 50 (to 12 mice) or 500 µg/kg (to 6 mice) of LPS3 was given to the mice Intravenously as a solution in physiological saline. The control group (10 mice) received only physiological saline. Two hours later, 10 mg/kg of naloxone was given lntraperitoneally, and immediately thereafter the jumping frequency of the mlce was counted over a period of 40 minutes. The results are shown in Table 8 as an average per mouse in the respective groups.

TABLE 8

| Dose of LPS3 (µg/kg) | 0 | 0.5 | 5 | 15 | 50 | 500 |
| --- | --- | --- | --- | --- | --- | --- |
| Jumping frequency | 69.5 | 36.8 | 42.0 | 16.1 | 20.5 | 11.5 |

Figure 3:
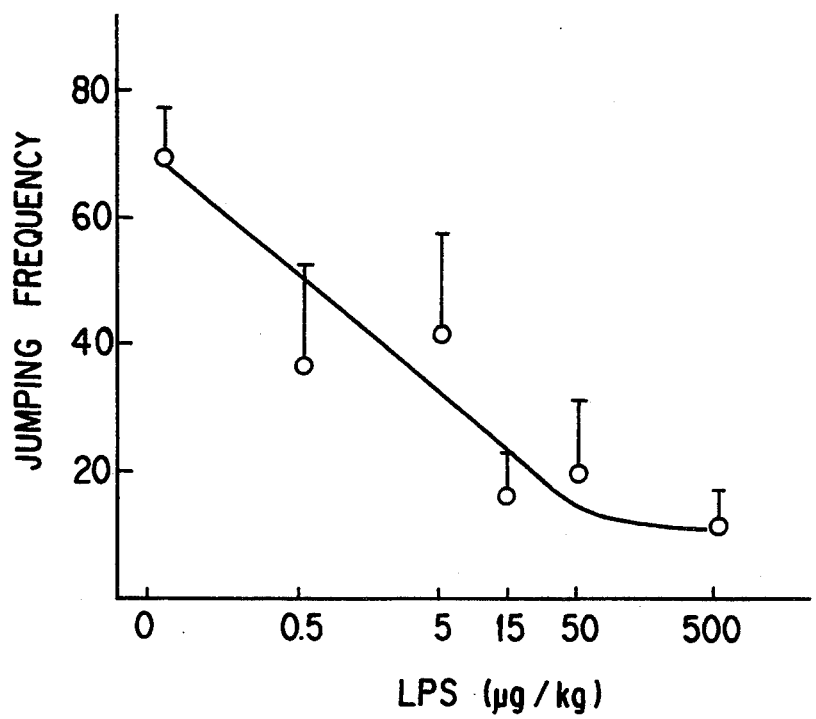
FIG. 3 is a graph showing the dose-dependent antiwithdrawal effects of the LPSs of the present invention in intravenous administration.

FIG. 3 is a graph corresponding to the results given in Table 8.

Experiment 5 (Antiwithdrawal effect - 3)

In order to determine whether the antiwithdrawal effects of the LPSs of the present invention in intradermal administration are dose-dependent, the procedures of Experiment 4 were followed except that the dose of LPS3 was 50 (to 7 mice) or 500 µg/kg (to 5 mice), and the control group consisted of 8 mice. The results are shown in Table 9 as an average per mouse in the respective groups.

TABLE 9

| Dose | Physiological saline | 50 µg/kg | 500 µg/kg |
| --- | --- | --- | --- |
| Frequency | 84.7 | 44 | 19.8 |

Figure 4:
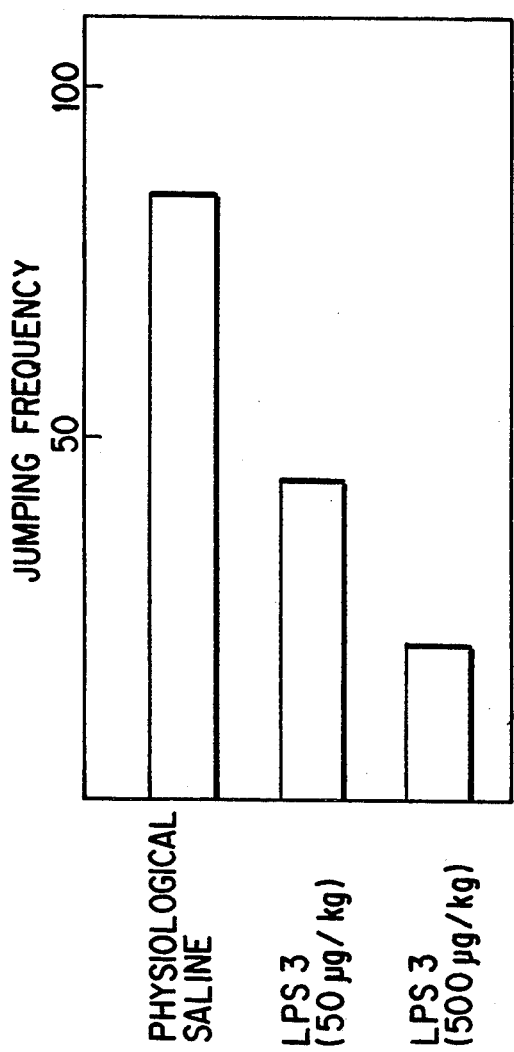
FIG. 4 is a graph showing the dose-dependent antiwithdrawal effects of the LPSs of the present invention In subcutaneous administration.

FIG. 4 is a graph corresponding to the results given in Table 9.

FIGS. 3 and 4 clearly show that the antiwithdrawal effects of the LPSs of the present invention are dose-dependent.

Experiment 6 (Antiwithdrawal effect - 4)

In order to determine whether the antiwithdrawal effects of the LPSs of the present invention are dose time-dependent, 12.7 mg of morphlne pellet prepared as in Experiment 3 was implanted in the back, a little below the neck, of 4 to 5 week old ddY mice (body weight: 20-24 g). Two days later, there was given 10 mg/kg of naloxone intraperitoneally. 50 µg/kS of LPSS was administered to the mice 1 hour (7 mice), 3 hours (8 mice), 8 hours (6 mice) or 18 hours (5 mice) before the administration of naloxone. Immediately after the administration of naloxone, the jumping frequency of the mice was counted over a period of 40 minutes. The control group receiving no LPS3 consisted of 9 mine. The results are shown in Table 10 as an average per mouse in the respective groups.

TABLE 10

| Administration time of LPS3 | No dose | Hrs. prior to naloxone administration | | | |
| --- | --- | --- | --- | --- | --- |
|  |  | 1 | 3 | 8 | 18 |
| Jumping frequency | 65.1 | 2.7 | 25.1 | 33.7 | 54.6 |

Figure 5:
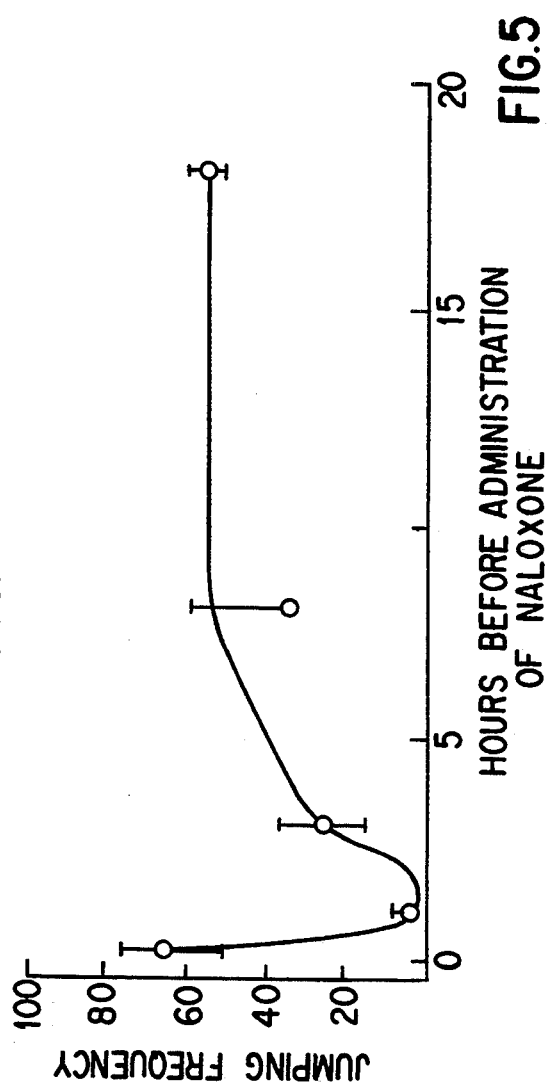
FIG. 5 is a graph showing the administration time-dependent withdrawal-preventive effects of the LPSs of the present invention.

FIG. 5 is a graph corresponding to the results given in Table 10. FIG. 5 teaches that the LPSs of the present invention have withdrawal-preventive effects, and the maximal preventive effects will be shown when the LPSs are administered immediately before the occurrence of withdrawal symptoms.

Dose, Interval and Toxicity

In view of the nature of immunity stimulators, analgesics and withdrawal agents, and veterinary immunostimulants, analgesics and withdrawal agents, the dose and the interval of the LPSs of the present invention are of course determined by the doctor or veterinarian In charge individually in view of the age, conditions, etc or the patient and effects of administration. However, it may be said that 1 µg–100 mg (oral administration), 10 ng–10 mg (intravenous administration) and 100 ng–1 mg (percutanous administration) are standard single dose per day to adults (body weight 60 kg). For veterinary use, about one sixtieth of the above quantities may be given per 1 kg of body weight of large-sized animals such as cattle, horses or the like. About twice as much as the dose to large-sized animals may be given per 1 kg of body weight of medium- or small-sized animals such as pigs, dogs, cats or the like. Fowls or the like may receive twice as much as the dose to medium- or small-sized animals. The $LD_{50}$ of LPS1, LPS2 and LPS3 in 7 week old C3H/He male mice having an average body weight of 22 g were 150, 180 and 180 µg/mouse according to the Behrens Karber; these values are less than 60% of 300 µg/mouse found for E. coli LPS. Further, E. coli LPS and B. P. LPS had the following $LD_{50}$ (an average of the data on two male BALB/C mice weighing 45 kg on average).

|  | $LD_{50}$/kg (mg) | |
| --- | --- | --- |
| LPS | i.v. | i.c. |
| E. coli LPS | 3.4 | 16 |
| B.P. LPS | 11 | 32 |

What we claim is:

1. A lipopolysaccharide produced by a strain of the species Serratia ficaria, having all of the identifying characteristics of FERM BP-3509 and exhibiting a dominant molecular weight of 5,000±1,000 as determined by SDS-PAGE method, having 2±1 phosphorus, 9±1 hexoeamines and 2±1 KDO per molecular weight of 5,000, wherein the identifying characteristics are as follows:

a) Morphological characteristics
   1) Small rod
   2) No Motility
   3) Gram stain: —
b) Growth
   1) Standard agar medium: A yellow to creamy round opaque colony is formed;
   2) SS agar medium: A white translucent colony is formed;
   3) TSI agar medium: No change is found on the slant, but a higher layer changes to yellow; Gas is produced.
c) Physiological characteristics
   1) Voges-Proskauer reaction: +
   2) Indole production: —
   3) Hydrogen sulfide production: —
   4) Utilization of citrate: +
   5) Urease: —
   6) Oxidass: —
   7) O-F test: +
d) Utilization of carbon sources
   1) Lactose: +
   2) Adonitol: —
   3) Rhamnose: +
   4) Mannitol: +
   5) Esculin: +
   6) Inositol: —
   7) Sorbitol: +
   8) Arabinose: +
   9) Raffinose: +
   10) Sucrose: +
e) Others
   1) Lyein decarboxylase: —
   2) Utilization of malonate: —
   3) Arginine dihydroxylase: —
   4) Phenylalanine deaminase: —
   5) Ornithine decarboxylase: —

2. A lipopolysaccharide produced by a strain of the species *Enterobacter cloacae*, having all of the identifying characteristics of FERM BP-3510 and exhibiting a dominant molecular weight of $6,500 \pm 2,500$ as determined by SDS-PAGE method, having 1-2 phosphorus, $7 \pm 1$ hexosamines and 1-2 KDO per molecular weight of 5,000, wherein the identifying characteristics are as follows:
a) Morphological characteristics
   1) Small rod
   2) No Motility
   3) Gram stain: —
b) Growth
   1) Standard agar medium: A creamy opaque colony is formed;
   2) SS agar medium: A red opaque colony is formed;
   3) TSI agar medium: No change is found on the slant, but a higher layer changes to yellow; Gas is produced;
c) Physiological characteristics
   1) voges-Proskauer reaction: +
   2) Indole production: —
   3) Hydrogen sulfide production: —
   4) Utilization of citrate: +
   5) Urease: —
   6) Oxidase: —
   7) O-F test: +
d) Utilization of carbon sources
   1) Lactose: +
   2) Adonitol: —
   3) Rhamnose: +
   4) Mannitol: +
   5) Esculin: +
   6) Inositol: —
   7) Sorbitol: +
   8) Arabinose: +
   9) Raffinose: +
   10) Sucrose: +
e) Others
   1) Lyein decarboxylase: —
   2) Utilization of malonate: +
   3) Arginine dihydroxylase: +
   4) Phenylalanine deaminase: —
   5) Ornithine decarboxylase: +

3. A lipopolysaccharide produced by a strain of the species *Pantoea agglomerans*, having all of the identifying characteristics of FERM BP-3511 and exhibiting a dominant molecular weight of $6,500 \pm 2,500$ as determined by SDS-PAGE method, having $2 \pm 1$ phosphorus, $5 \pm 1$ hexosamines and $2 \pm 1$ KDO per molecular weight of 5,000, wherein the identifying characteristics are as follows:
a) Morphological characteristics
   1) Small rod
   2) No Motility
   3) Gram stain: —
b) Growth
   1) Standard agar medium: A yellow round translucent colony is formed;
   2) SS agar medium: No colony is formed;
   3) TSI agar medium: No change is found on the slant, but a higher layer changes to yellow. Gas is not produced;
c) Physiological characteristics
   1) Voges-Proskauer reaction: +
   2) Indole production: —
   3) Hydrogen sulfide production: —
   4) Utilization of titrate: +
   5) Urease: —
   6) Oxidass: —
   7) O-F test: +
d) Utilization of carbon sources
   1) Lactose: +
   2) Adonitol: —
   3) Rhamnose: +
   4) Mannitol: +
   5) Esculin: +
   6) Inositol: —
   7) Sorbitol: +
   8) Arabinose: +
   9) Raffinose: —
   10) Sucrose: +
e) Others
   1) Lysin decarboxylase: —
   2) Utilization of malonate: +
   3) Arginine dihydroxylase: —
   4) Phenylalanine deaminase: —
   5) Ornithine decarboxylase: —

4. An immunostimulant comprising the lipopolysaccharide of claim 1, together with a pharmaceutically or veterinarily acceptable carrier.

5. An immunostimulant comprising the lipopolysaccharide of claim 2, together with a pharmaceutically or veterinarily acceptable carrier.

6. An immunostimulant comprising the lipopolysaccharide of claim 3, together with a pharmaceutically or veterinarily acceptable carrier.

* * * * *